United States Patent
Dalke et al.

[11] Patent Number: 5,957,137
[45] Date of Patent: Sep. 28, 1999

[54] CONTROLLED DILUTION CONTROLLED CONCENTRATION CARDIOPLEGIA SOLUTION ADMINISTRATION

[75] Inventors: William D. Dalke, Aurora; Bruce S. Ellingboe, Littleton, both of Colo.

[73] Assignee: COBE Cardiovascular Operating Co., Inc., Arvada, Colo.

[21] Appl. No.: 08/997,367

[22] Filed: Dec. 23, 1997

[51] Int. Cl.$^6$ .................................................. A61B 19/00
[52] U.S. Cl. ............................................... 128/898; 604/4
[58] Field of Search .................................. 128/898; 604/4

[56] References Cited

U.S. PATENT DOCUMENTS

| | | |
|---|---|---|
| 4,116,589 | 9/1978 | Rishton . |
| 4,416,280 | 11/1983 | Carpenter et al. . |
| 4,512,163 | 4/1985 | Wells et al. . |
| 4,568,330 | 2/1986 | Kujawski et al. . |
| 4,883,455 | 11/1989 | Leonard . |
| 4,943,277 | 7/1990 | Bolling . |
| 5,011,469 | 4/1991 | Buckberg et al. . |
| 5,013,303 | 5/1991 | Tamari et al. . |
| 5,115,682 | 5/1992 | Feiler . |
| 5,269,749 | 12/1993 | Koturov . |
| 5,388,634 | 2/1995 | Weinstein et al. . |
| 5,423,749 | 6/1995 | Merte et al. . |
| 5,423,769 | 6/1995 | Jonkman et al. . |
| 5,466,216 | 11/1995 | Brown et al. . |
| 5,499,665 | 3/1996 | Sollevi . |
| 5,653,681 | 8/1997 | Ellingboe . |

*Primary Examiner*—John G. Weiss
*Assistant Examiner*—William Noggle
*Attorney, Agent, or Firm*—Popovich & Wiles, P.A.

[57] ABSTRACT

A method and apparatus for preparing a cardioplegia mixture is provided which allows an increased level of control over the flow rate, dilution ration and concentration of cardioplegia inducing components in cardioplegia mixture during cardiovascular surgery. The method for preparing the cardioplegia mixture includes the steps of combining first and second crystalloid solutions of different concentrations to establish a total volume flow rate of combined solutions. The flow rate of the first crystalloid solution is self adjusted to equal the established total volume flow rate minus the established volume flow rate of the second crystalloid solution. The apparatus for preparing a cardioplegia mixture includes first and second crystalloid solutions containing a cardioplegia inducing component at different concentrations, and means for flowing and combining the solutions and establishing a total volume flow rate of the combined solution. The apparatus further includes means for self-adjustment of the flow rate of the first crystalloid solution to equal total the volume flow rate minus the established volume flow rate of the second crystalloid solution. The apparatus preferably includes a disposable tubing set for flowing, combining, and interconnecting the crystalloid solutions.

18 Claims, 7 Drawing Sheets ly 5,957,137

CONTROLLED DILUTION CONTROLLED CONCENTRATION CARDIOPLEGIA SOLUTION ADMINISTRATION

FIELD OF THE INVENTION

The invention relates to the infusion of a composition into a bodily fluid. More particularly it relates to the controlled infusion of crystalloid solution into blood during cardiovascular surgery.

BACKGROUND OF THE INVENTION

During cardiovascular surgery and cardiac valve surgery (commonly known as open heart surgery) it is often necessary to arrest the pumping activity of the heart by inducing heart paralysis or "cardioplegia." While the heart is arrested it is also necessary to replace or supplement the heart and lungs by means of a cardiopulmonary support circuit (commonly known as a heart-lung machine). The cardiopulmonary support circuit receives blood from a major vessel entering the heart, such as the vena cava. The blood received from the heart is typically transported to a venous reservoir and then pumped through an oxygenator by an arterial pump and transported back to the patient via an arterial line, to enter the patient through a major vessel leaving the heart, such as the aorta. The pumping action of the arterial pump temporarily replaces the action of the heart and the oxygenator temporarily replaces the action of the lungs. It is thereby possible to deliver oxygenated blood to the tissues of the patient during the open heart surgery while the patient's heart is stopped. The cardiopulmonary circuit typically also includes a cardioplegia circuit, a cardiotomy circuit and a ventricular vent circuit. The cardiopulmonary circuit is typically operated in the operation room by a medical professional known as a "perfusionist."

The cardioplegia circuit delivers a cardioplegia mixture to the heart. The cardioplegia mixture discontinues the beating of the heart in a manner that minimizes damage to the heart's myocardium and renders the heart motionless so that a surgeon may operate. Cardioplegia mixture may also supply other ingredients to provide for myocardial protection. Cardioplegia mixture may comprise a crystalloid solution delivered alone or may also include oxygenated blood diverted from the arterial line. The crystalloid solution typically contains potassium chloride (KCl), sugars and magnesium. The potassium cation ($K^+$) concentration in the cardioplegia is initially elevated, for example 25 mmol/l during induction of arrests, and thereafter reduced, for example 8.5 to 9.0 mmol/l, during the remainder of the procedure. Other cations, such as magnesium ($Mg^{++}$) can be used as heart arresting agents.

It is generally preferred to include oxygenated blood, diverted from an arterial portion of the cardiopulmonary support circuit, in the cardioplegia mixture, so that the cardioplegia mixture is buffered and can oxygenate the myocardium. Where the cardioplegia mixture includes diverted arterial blood the cardioplegia circuit typically comprises diverted blood tubing, for containing blood diverted from an arterial blood line, a crystalloid solution bag and tubing, a cardioplegia delivery tubing conveying the mixture of blood and crystalloid solution, and one or more pumps, which are typically peristaltic pumps.

The crystalloid solution tubing and the diverted blood tubing may both comprise pump headers which may both be threaded through the same peristaltic pump or through different peristaltic pumps. The pumps may be other pump types as are known in the art.

The cardioplegia mixture is generally cooled to render it hypothermic, further protecting the myocardium during open heart surgery. The cardioplegia mixture may be administered antegrade, directly into the coronary ostia of the heart, or retrograde, through the right atrium or the coronary sinus, depending upon the surgical need. The cardioplegia mixture is then distributed through the circulatory system of the patient in combination with the blood perfused into the aorta or, occasionally, it may be withdrawn from the chest cavity and discarded or directed via a cardiotomy line to the cardiopulmonary support circuit.

In one prior art system, a peristaltic cardioplegia pump is provided to pump diverted arterial blood from the arterial blood line for combination with crystalloid solution, which is pumped by a separate crystalloid pump. The diverted arterial blood pumped by the cardioplegia pump and the crystalloid solution pumped by the crystalloid pump are combined downstream of the pumps to create the cardioplegia mixture. By controlling the speeds, and hence the pumping rates, of the crystalloid pump and the cardioplegia pump the perfusionist can control a flow rate of crystalloid solution and the flow rate of diverted arterial blood, thereby controlling both the total flow of cardioplegia mixture and the concentration of crystalloid solution in the cardioplegia mixture, that is a ratio of crystalloid solution to diverted arterial blood. In this prior art system, it is possible to control the concentration of crystalloid in the cardioplegia mixture, but the dilution of the diverted arterial blood by the crystalloid solution depends on the proportion of crystalloid solution. That is, as the proportion of crystalloid solution is increased, the dilution of the diverted arterial blood is also increased. This is important because dilution of the diverted arterial blood decreases the proportion of red blood cells, the oxygen carrying component of the arterial blood, reducing the cardioplegia mixture's ability to deliver oxygen to the tissues of the myocardium. A further undesirable consequence of cardioplegia mixture administration is dilution of the total blood volume of the patient. It is, therefore, desirable to control and limit this dilution during surgery. This dilution can be controlled by use of a hemoconcentrator, as is well known, but such hemoconcentrators increase the cost and complexity of the cardiopulmonary circuit. Concentrations of other ingredients in the crystalloid solution vary with the potassium concentration in the mixture. It may be desirable to keep other concentrations fixed while varying only the potassium concentration.

Another prior art system employs a cardioplegia pump which is a peristaltic pump having two pump headers tube in the same raceway. One pump header tube carries the diverted arterial blood and the other carries the crystalloid solution from the source of crystalloid solution. The ratio of the two pump headers is selected to fix the dilution of the diverted arterial blood at a constant value. Changes in potassium concentration are achieved by switching bags of crystalloid solution. The heart is typically arrested with a high concentration solution, then the bag is switched to a lower concentration for maintenance of arrest. In this prior art system, the volume of cardioplegia mixture delivered to the heart is increased and decreased in order to increase and decrease the amount of crystalloid delivered to the heart.

It is desired to provide a cardioplegia delivery system that allows the potassium concentration in the cardioplegia mixture to be varied over a desired range without varying the dilution of the cardioplegia mixture or the concentration of other ingredients. Alternatively, it is desired to permit variation of the potassium and/or other concentrations, while independently varying the degree of dilution and the total flow of cardioplegia mixture to the patient's heart. Varying the potassium concentration in the cardioplegia mixture would allow the perfusionist to minimize the total amount of potassium added to the patient's blood during an operation. It would also allow a high initial potassium concentration to rapidly arrest the heart followed by a lower concentration to maintain arrest. It is further desired to allow for adjustment of the amount of potassium added to the blood to compensate for the increase in the patient's serum potassium level throughout the course of the operation. It is also desired to increase the cardioplegia potassium concentration in the event of a reoccurrence of heart activity during surgery.

U.S. Pat. No. 5,385,540 to Abbott et al., appears to disclose cardioplegia systems which include two crystalloid solutions which can be administered alternatively, allowing two concentrations of cardioplegia to be administered, but not permitting continuous variation of the cardioplegia solution concentration. U.S. Pat. No. 5,385,540 also appears to disclose a system in which cardioplegia crystalloid solution is injected into a crystalloid cardioplegia mixture downstream of a cardioplegia pump. Such a system permits control of the concentration of crystalloid in the cardioplegia mixture but also would vary the dilution of the cardioplegia mixture by the crystalloid solution.

U.S. Pat. No. 5,322,500 to Johnson, et al., appears to disclose a system utilizing two sources of cardioplegia solution which are alternatively selectable.

U.S. Pat. No. 5,358,481 to Todd et al, appears to disclose a variable concentration cardioplegia system in which a plurality of alternatively selectable crystalloid pump headers are placed in the same peristaltic pump raceway with the diverted arterial blood pump header, thereby permitting incremental adjustment of cardioplegia concentrations and dilution of the cardioplegia mixture. However, the dilution of the cardioplegia mixture would be a direct function of the concentration of the crystalloid solution added by selective operation of the alternatively selectable pump headers.

None of the known prior art systems permit continuous variation of crystalloid solution component concentration, and, in particular, potassium concentration in the cardioplegia mixture while maintaining either a fixed dilution ratio between the crystalloid solution and the diverted arterial blood in the cardioplegia mixture. Further, none of the known prior art systems allow control of the dilution ratio independent from control of the concentration of crystalloid in the mixture.

It is against this background that the significant improvements in the art of cardioplegia mixture delivery and open heart surgery of the present invention occurred.

SUMMARY OF INVENTION

A significant aspect of the present invention is a method and apparatus, including a disposable tubing set, for preparing a cardioplegia mixture which permits the perfusionist or supervising cardiovascular surgeon to exercise an increased level of control over the flow rate, dilution ratio and concentration of cardioplegia-inducing components in cardioplegia mixture.

In accordance with this aspect of the invention, the method of preparing the cardioplegia mixture comprises providing a first source of a first crystalloid solution which includes a cardioplegia inducing component at a concentration and providing a second source of a second crystalloid solution which includes the cardioplegia inducing component at a different concentration than the concentration in the first crystalloid solution. The first crystalloid solution is caused to flow from the first source of crystalloid solution, the second crystalloid solution is caused to flow from the second source of crystalloid solution, the flowing first crystalloid solution being combined with the flowing second crystalloid solution. A total volume flow rate of the combined first and second crystalloid solutions from the first and second sources of crystalloid solution is established and a volume flow rate of the second crystalloid solution from the second source of crystalloid solution is established, with the flow rate of first crystalloid solution from the first source of crystalloid solution being allowed to self adjust to be equal to the established total volume flow rate minus the established volume flow rate of the second crystalloid solution.

Further in accordance with this aspect of the invention the apparatus for preparing a cardioplegia mixture comprises a first source of a first crystalloid solution which includes a cardioplegia inducing component at a concentration and a second source of a second crystalloid solution which includes the cardioplegia inducing component at a different concentration than the concentration in the first crystalloid solution. The apparatus further includes means for flowing first crystalloid solution from the first source of crystalloid solution, means for flowing second crystalloid solution from the second source of crystalloid solution and means for combining the flowing first crystalloid solution with the flowing second crystalloid solution. Means are provided for establishing a total volume flow rate of the combined first and second crystalloid solutions from the first and second sources of crystalloid solution, for establishing a volume flow rate of the second crystalloid solution from the second source of crystalloid solution, and for allowing the flow rate of first crystalloid solution from the first source of crystalloid solution to self adjust to be equal to the established total volume flow rate minus the established volume flow rate of the second crystalloid solution.

Still further in accordance with this aspect of the invention, the apparatus for preparing a cardioplegia mixture comprises a first container for containing a first crystalloid solution which includes a cardioplegia inducing component at a first concentration; and a second container for containing a second crystalloid solution which includes the cardioplegia inducing component at a second concentration different than the concentration in the first crystalloid solution. A crystalloid solution mixing junction is provided to which the first container is connected by first crystalloid solution tubing and to which the second container is connected by second crystalloid solution tubing. A crystalloid solution concentration control pump is configured and located to establish and control a flow of second crystalloid solution in the second crystalloid solution tubing. A blended crystalloid solution tubing extends from the crystalloid solution mixing junction and is in flow communication with the heart in which cardioplegia is to be induced. A pump is located and configured to establish and control a flow of blended first and second crystalloid solution through the blended crystalloid solution tubing.

Still further yet in accordance with this aspect of the invention, the apparatus includes a disposable tubing set for preparation of a cardioplegia mixture comprising a first container connector for connection to a first crystalloid solution container and a second container connector for connection to a second crystalloid solution container. A first crystalloid solution tubing interconnects the first container connector to a crystalloid solution mixing junction and a second crystalloid solution tubing interconnects the second container connector to the crystalloid solution mixing junction. The second crystalloid solution tubing includes a tubing segment adapted for insertion into the raceway of a peristaltic pump. A cardioplegia mixture mixing junction joins the blended crystalloid solution tubing to an arterial blood diversion tubing. The arterial blood diversion tubing and the blended crystalloid solution tubing each include a tubing segment adapted for insertion into the raceway of a single common peristaltic pump, the diameters of said tubing segments being selected to establish a fixed ratio between the flow in the arterial blood diversion tubing and the flow in the crystalloid solution tubing. Further aspects of the present invention will be apparent to those skilled in the art from the following detailed description and the claims.

DETAILED DESCRIPTION OF THE PREFERRED EMBODIMENT

Reference will now be made in detail to the preferred embodiment of the present invention, examples of which are illustrated in the accompanying FIGS. 1–7. Where possible, the same or analogous reference numbers will be used throughout the drawings to refer to the same or analogous parts.

Figure 1:
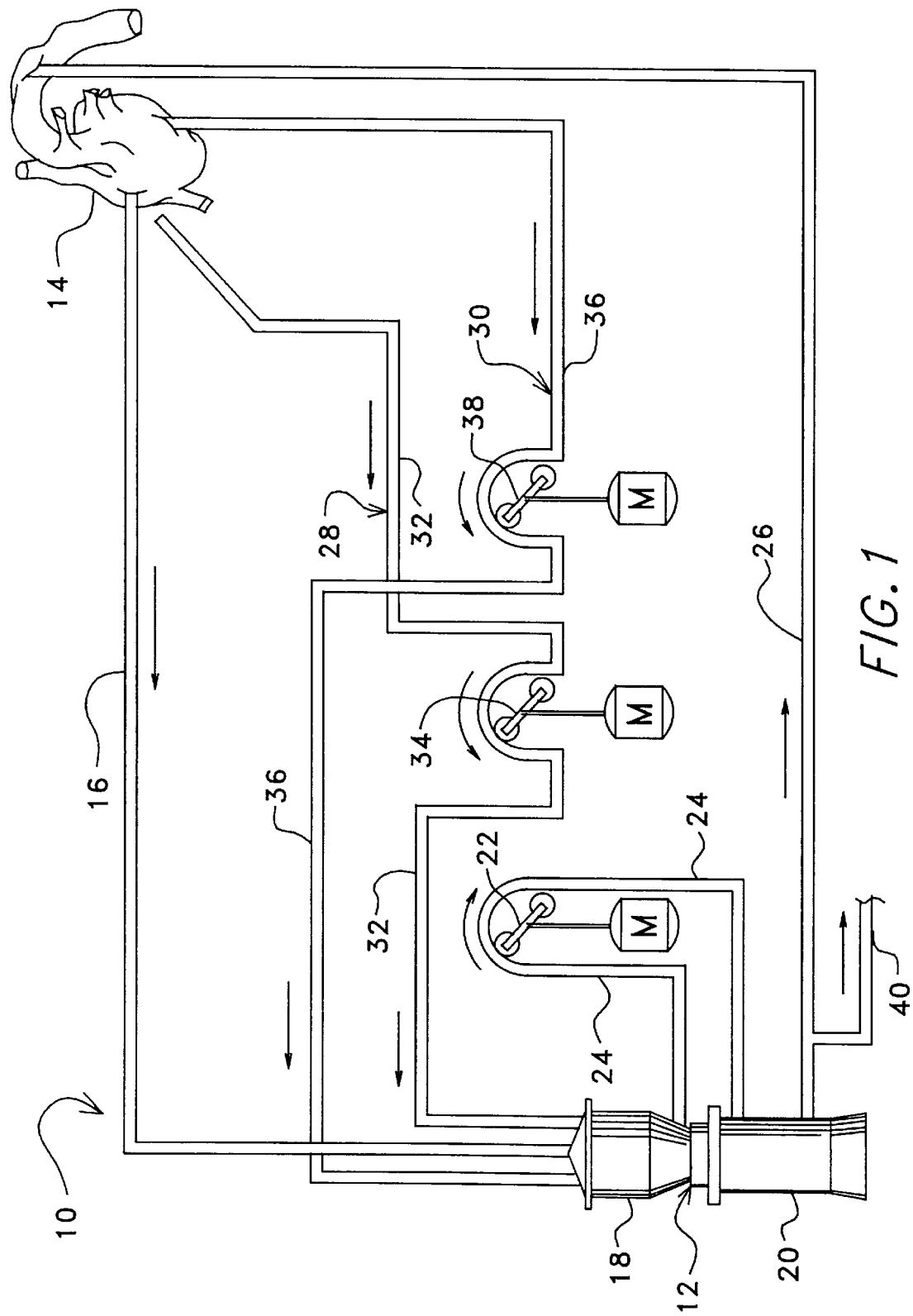
FIG. 1 is a schematic representation of an exemplary cardiopulmonary support circuit with which the present invention may be used.

FIG. 1 illustrates schematically an exemplary cardiopulmonary circuit 10 with which the present invention may be used. It will be apparent to one skilled in the art that the present invention may be used with any cardiopulmonary circuit, of which several variations in equipment and detail are possible, while still being within the scope of the present invention.

The exemplary cardiopulmonary circuit 10 comprises a plurality of tubings, commonly referred to as lines, of the typical flexible plastic medical tubing type, in combination with an oxygenator apparatus 12, as is well known, along with other devices, arranged and configured to replace the pumping action of a heart 14 and lungs (not shown) of a patient (not shown) undergoing open heart surgery in which it is necessary to arrest the heart 14 temporarily in order to perform the surgery. The cardiopulmonary circuit 10 comprises a venous tubing 16 which receives blood from a major blood vessel entering the heart 14, such as one of the vena cava. The venous tubing 16 conveys the venous blood from the heart 14 to the oxygenator apparatus 12.

An exemplary oxygenator apparatus 12 comprises a combination venous reservoir and cardiotomy reservoir 18 and an oxygenation and heat exchange section 20. Venous blood is withdrawn from the venous and cardiotomy reservoir 18 by an arterial blood pump 22 through an arterial blood pump tubing 24. The arterial blood pump 22 may be of the well known peristaltic type, or may alternatively be a centrifugal pump, a diaphragm pump or any other of several well-known types of fluid pumps. The arterial blood pump tubing 24 conveys the venous blood to the oxygenation and heat exchange section 20 of the oxygenator apparatus 12, where the venous blood is processed by oxygenating the blood and concurrently removing carbon dioxide from the blood and adjusting the temperature of the blood, thereby converting the "venous" blood to "arterial" blood.

The arterial blood is then conveyed by the pumping force of the arterial pump 22 through an arterial blood tubing 26 to a major vessel leaving the heart 14 of the patient (not shown) such as the aorta.

The cardiopulmonary circuit 10 may also comprise a cardiotomy sub-circuit 28 and a left ventricle vent sub-circuit 30.

The cardiotomy sub-circuit 28 conveys cardiotomy blood from the chest cavity 14 to the venous and cardiotomy reservoir 18 or, alternatively, to a separate cardiotomy reservoir (not shown) and from there to the venous reservoir 18. The cardiotomy sub-circuit 28 typically comprises a cardiotomy tubing 32 and a cardiotomy pump 34 for moving the cardiotomy blood through the cardiotomy tubing 32 from the heart 14 to the venous and cardiotomy reservoir 18.

The left ventricle vent sub-circuit 30 comprises a left ventricle vent tubing 36 and a left ventricle vent pump 38 for conveying vented blood from the left ventricle of the heart 14 to the venous and cardiotomy reservoir 18.

An arterial blood diversion tubing 40 may be connected to the arterial blood tubing 26 at a point intermediate the oxygenation and heat exchange section 20 of the oxygenator apparatus 12 and the heart 14 of the patient. The arterial blood diversion tubing 40 permits diversion of arterial blood for use by a cardioplegia sub-circuit.

The cardiopulmonary circuit 10 may comprise numerous variations and may further comprise additional tubings and components, such as, by way of example and not limitation, separate cardiotomy reservoirs, arterial filters, hemoconcentrators, pressure and temperature monitoring devices, air detectors and traps, valves, etc. Further, the oxygenator apparatus, which is illustrated herein as an integrated hard shell venous and cardiotomy reservoir 18 and oxygenation and heat exchange section 20 may comprise multiple components separately mounted and connected, and the reservoir 18 may be a bag type reservoir. Furthermore, the circuit illustrated is typical for a microporous membrane oxygenation section 20. The present invention is also useful in conjunction with cardiopulmonary circuits which utilize the well known homogeneous membrane type oxygenator or the well known bubble type oxygenator. Further, the present invention may be used with cardiopulmonary circuits which employ an arterial reservoir in addition to or instead of the venous reservoir 18.

Figure 2:
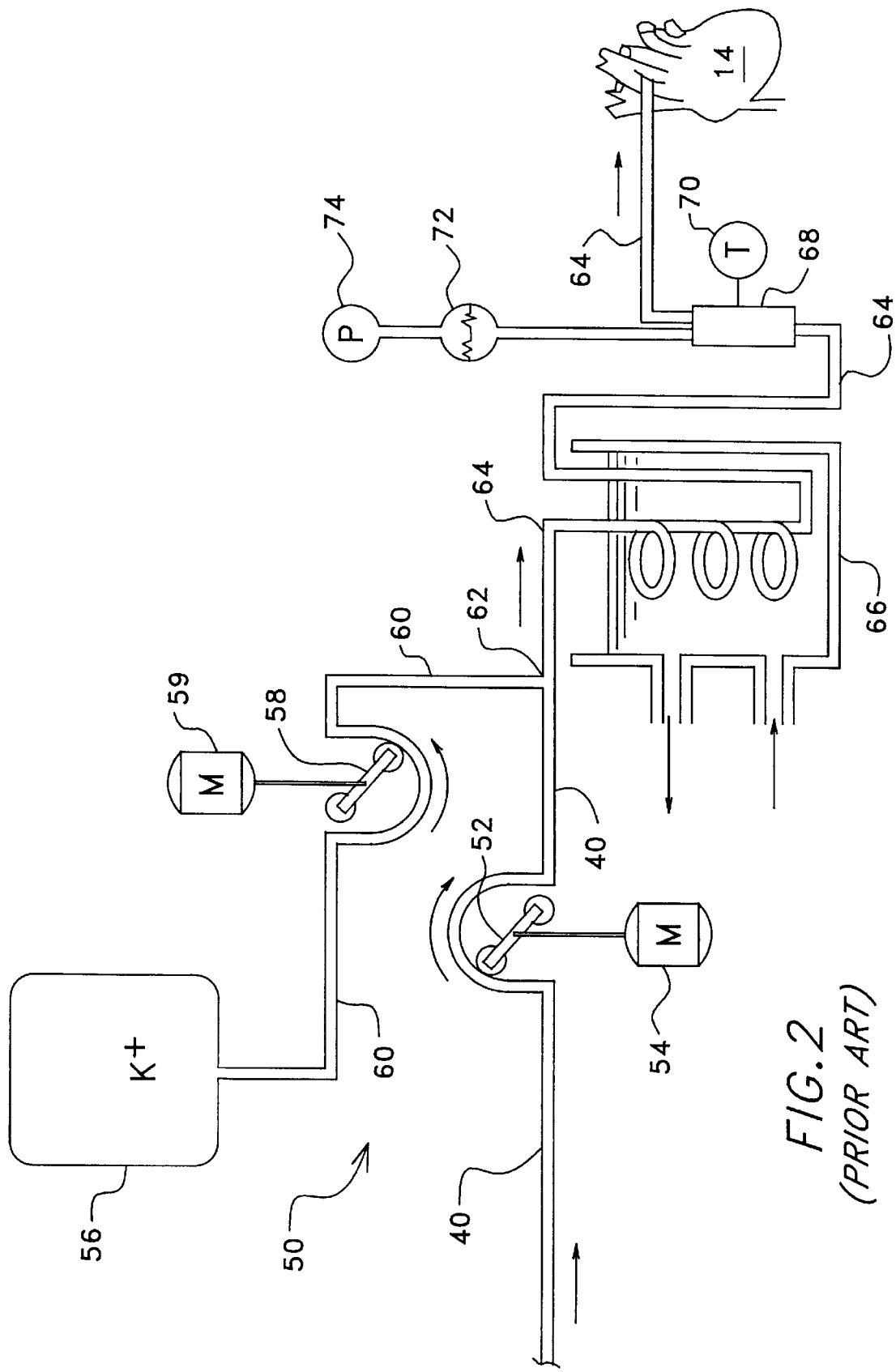
FIG. 2 is a schematic representation of a cardioplegia mixture delivery system of the prior art.

FIG. 2 schematically illustrates a prior art cardioplegia circuit 50. The prior art cardioplegia circuit 50 comprises a cardioplegia pump 52 which may be of the typical peristaltic pump type or any other suitable type. The cardioplegia pump 52 propels and controls the volume flow rate of blood diverted through arterial blood diversion tubing 40 to the cardioplegia circuit 50. The rate at which diverted arterial blood flows through the arterial blood diversion tubing 40 and thus the volume flow rate of blood, can be established by adjusting the rotative speed of a cardioplegia pump motor 54 which drives the cardioplegia pump 52. A source of crystalloid solution 56 is provided. The crystalloid solution typically contains potassium chloride (KCl), sugars and magnesium and may contain a variety of other ingredients. The KCl, and in particular the potassium ($K^+$) cation of the KCl, is typically the agent which arrests the heart and maintains the heart in a arrested state. Alternatively, other cations such as magnesium ($Mg^{++}$) could be used as the heart arresting agent. The source of crystalloid solution 56 is typically a medical solution bag of known type. A crystalloid pump 58 of any known type, preferably a peristaltic pump, propels and controls the volume of flow rate of crystalloid solution from the source of crystalloid solution 56 through a crystalloid tubing 60 to a mixing junction 62 where the arterial blood diversion tubing 40 joins the crystalloid tubing 60 downstream of both the crystalloid pump 58 and the cardioplegia pump 52. The rate at which crystalloid solution flows through the crystalloid tubing 60, and thus the volume flow rate of crystalloid, can be established by adjusting the rotative speed of a crystalloid pump motor 59 which drives the crystalloid pump 58. The crystalloid solution is mixed with the diverted arterial blood at the mixing point 62 to form a cardioplegia mixture. The cardioplegia mixture is conveyed from the mixing junction 62 through a cardioplegia tubing 64 to the heart 14 of the patient. The cardioplegia mixture may be administered to the patient's heart antigrade directly into the coronary ostia or retrograde through the right atrium or the coronary sinus, depending on the surgical need.

If the myocardial temperature is too high during the period of cardioplegia, ischemia may result, which in turn can cause heart tissue damage. Accordingly, a heat exchanger 66 is interposed in the cardioplegia tubing 64 to cool the cardioplegia mixture. The heat exchanger 66 may be of any known type. For example, the heat exchanger 66 may be of the type described in U.S. Pat. No. 5,269,749 to Koturov, assigned to the assignee of the present application, the disclosure of which is incorporated herein by reference. Other protective and monitoring devices may be interposed in the cardioplegia tubing 64. For example, a bubble trap 68 and associated temperature sensor 70, pressure isolation pod 72 and pressure sensor 74 are typically interposed in the cardioplegia tubing 64 following the heat exchanger 66. The rate of crystalloid solution flow through the crystalloid tubing 60 can be controlled by adjusting the rotative speed of a crystalloid pump motor 59 thereby adjusting the pumping rate of the crystalloid pump 58.

In operation, the perfusionist or an automatic control device (not shown) can control this prior art cardioplegia circuit 50 by adjusting the flow rate of the diverted arterial blood and the crystalloid solution independently. In this way, the perfusionist, or the control device can control the total volume flow rate of cardioplegia mixture flowing through the cardioplegia tubing 64 to the heart 14, which is the sum of the crystalloid solution volume flow rate flowing through the crystalloid tubing 60 and the diverted arterial blood volume flow rate flowing through the arterial blood diversion tubing 40. Further the perfusionist or control device can control the proportion of crystalloid solution to diverted arterial blood in the cardioplegia mixture by controlling the ratio of the speeds of the cardioplegia pump motor 54 and the crystalloid solution pump motor 59. The perfusionist or control device cannot, however, independently establish a fixed dilution ratio of cardioplegia solution volume to the diverted arterial blood flow volume while simultaneously independently controlling the concentration of crystalloid, and in particular the concentration of potassium, in the cardioplegia mixture. The amount of potassium delivered and the volume of crystalloid solution in the mixture, and thus the dilution of arterial blood, are directly proportional to each other.

Figure 3:
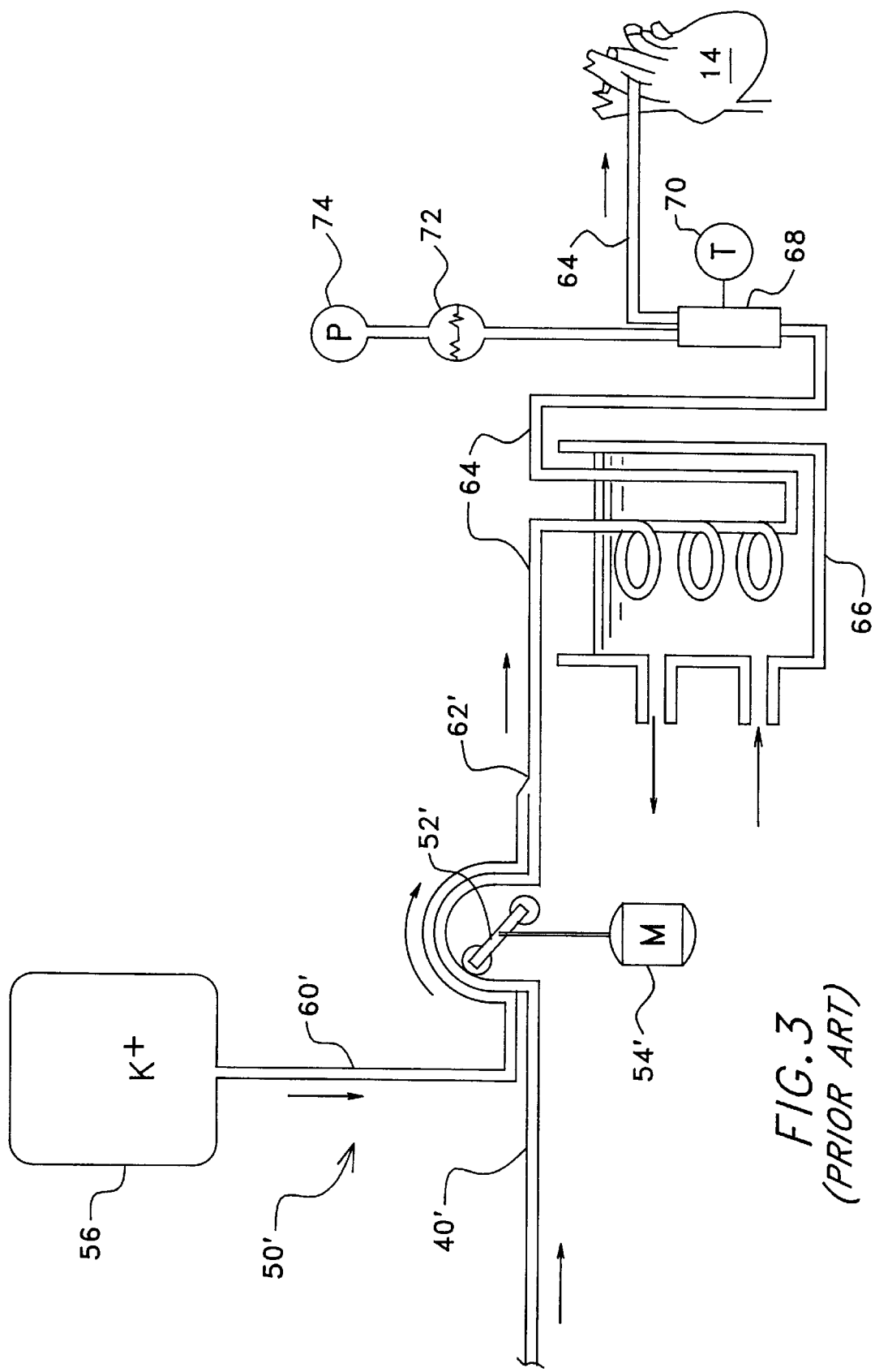
FIG. 3 is a schematic representation of another cardioplegia mixture delivery system of the prior art.

FIG. 3 schematically illustrates another prior art cardioplegia system 50'. The arterial blood diversion tubing 40' and the crystalloid tubing 60' are both placed in the single raceway of a cardioplegia pump 52' and joined at a mixing junction 62' from which the cardioplegia tubing extends to the heart 14'. The concentration of crystalloid solution in the cardioplegia mixture and thus the dilution of the cardioplegia mixture, is set as a fixed proportion of the cardioplegia mixture by the selection of the tubing sizes of the crystalloid tubing 60' and the arterial blood diversion tubing 40' where they pass through the raceway of the peristaltic cardioplegia pump 52'. The total amount of cardioplegia mixture and the delivery rate of crystalloid to the heart are controlled by the perfusionist or an automatic control device (not shown) by adjusting the rotative speed of a motor 54' which drives the cardioplegia pump 52'. The amount of crystalloid delivered is directly proportional to the amount of cardioplegia mixture delivered. Although the dilution ratio is controlled at a fixed ratio by the selection of tubing sizes, it is not possible to vary the concentration of crystalloid nor is it possible to change the amount of crystalloid delivered to the heart 14 without varying the volume of cardioplegia mixture delivered to the heart 14 and thus varying the volume of diverted arterial blood delivered to the heart 14.

Figure 4:
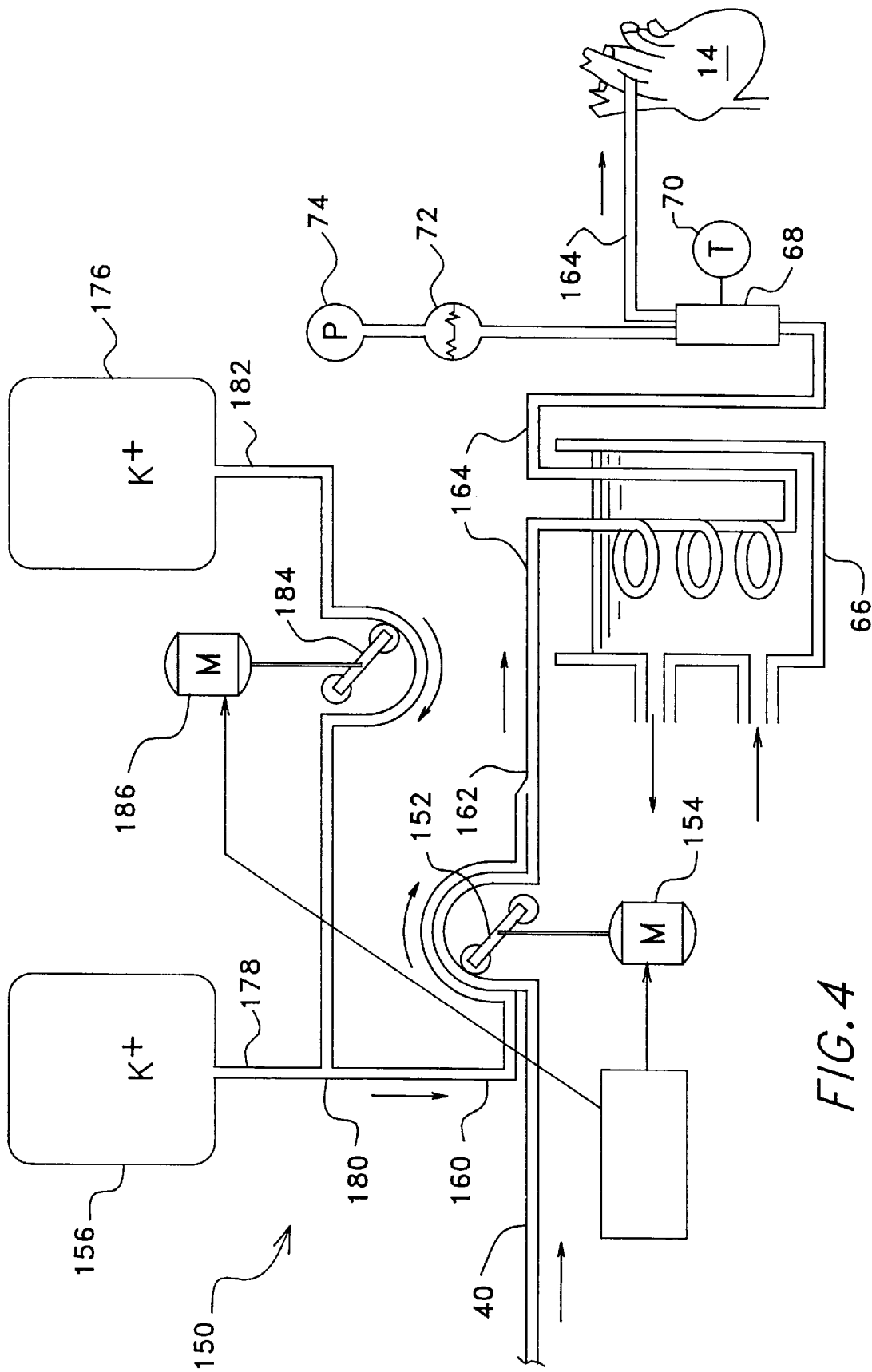
FIG. 4 is a schematic representation of a cardioplegia mixture delivery system in accordance with a preferred embodiment of the present invention.

FIG. 4 schematically illustrates a preferred embodiment of the present invention which overcomes many of the disadvantages of the prior art, as will be apparent to those skilled in the art, and provides the perfusionist and cardiovascular surgeon with a much greater degree of control over the quantity and composition of cardioplegia mixtures delivered to the heart 14. The cardioplegia circuit 150 of the present invention comprises the arterial blood diversion tubing 40 which conveys diverted arterial blood from the cardiopulmonary circuit 10 to the cardioplegia circuit 150. The arterial blood diversion tubing 40 passes through a raceway of a cardioplegia pump 152. The cardioplegia pump 152 is of the conventional peristaltic type and is driven by a cardioplegia pump motor 154.

It should be appreciated that venous, or unoxygenated, blood can also be conveyed to the cardioplegia circuit in all embodiments described herein.

A first, baseline source of crystalloid solution 156 is provided. The first source of crystalloid solution 156 may contain the typical sugars and magnesium found in crystalloid solution and KCl sufficient to deliver $K^+$ cations at the minimum anticipated desired concentration for the procedure. A second, concentration controlling, source of crystalloid solution 176 is also provided. The second source of crystalloid solution 176 includes the sugars and magnesium found in the first source 156, but contains KCl at a concentration higher than that found in the first source 156 of crystalloid solution. Each source of crystalloid solution 156, 176 may typically be a bag of solution as it is well known for medical solutions.

The first source of crystalloid solution 156 is connected by a first crystalloid tubing 178 to a crystalloid mixing junction 180. The second source of crystalloid solution 176 is connected to the crystalloid mixing junction 180 by a second crystalloid tubing 182. The second crystalloid tubing 182 is passed through the raceway of a crystalloid concentration control pump 184 which is driven by a crystalloid concentration control pump motor 186. The crystalloid concentration control pump 184 propels the flow of the second crystalloid solution from the second source of crystalloid solution 176 through the second crystalloid tubing 182 to the crystalloid mixing junction 180. Crystalloid solution from the first source 156 and the second source 176 are blended together at the crystalloid mixing junction 180.

Blended crystalloid solution is conveyed from the crystalloid mixing junction 180 through a blended crystalloid tubing 160 which passes through the raceway of the cardioplegia pump 152 together with the arterial blood diversion tubing 40 and joins the diverted arterial blood tubing 40 at a cardioplegia mixture mixing junction 162 which follows the cardioplegia pump 152.

The cardioplegia mixture is conveyed to the heart 14 from the cardioplegia mixture mixing junction 162 by a cardioplegia line 164 which has interposed in it a heat exchanger 66 and a bubble trap 68 with temperature monitor 70, pressure isolation pod 72 and pressure sensor 74 as previously described. Tubing diameters of the blended crystalloid tubing 160 and the arterial blood diversion tubing 40 are selected to establish a fixed ratio between the volume flow rate of the blended crystalloid solution and the diverted arterial blood, and thus establishing a fixed dilution ratio in the resulting cardioplegia mixture. The total flow rate of the cardioplegia mixture can then be established by the perfusionist or a control device 151 by adjusting the rotative speed of the cardioplegia motor 154 of the cardioplegia pump 152 as is well known. The control device 151 or perfusionist would limit the flow rate of the crystalloid concentration control pump 184 to be equal to or less than the flow rate of crystalloid in the blended crystalloid tubing 160 through the cardioplegia pump 152 to prevent flow of crystalloid solution from the second source of crystalloid solution 176 to the first source of crystalloid solution 156. The concentration of crystalloid in the blended crystalloid solution and thus in the cardioplegia mixture can be adjusted by the perfusionist or control device 151 by adjusting the rotative speed of the crystalloid concentration control pump motor 186. This permits variation of potassium or arresting agent delivery to the heart 14 without varying the dilution of the cardioplegia mixture and without varying the flow rate of the cardioplegia mixture. Thus, the present invention affords the perfusionist and the supervising cardiovascular surgeon with a greatly increased measure of control over the delivery of crystalloid solution during cardiovascular surgery.

Figure 5:
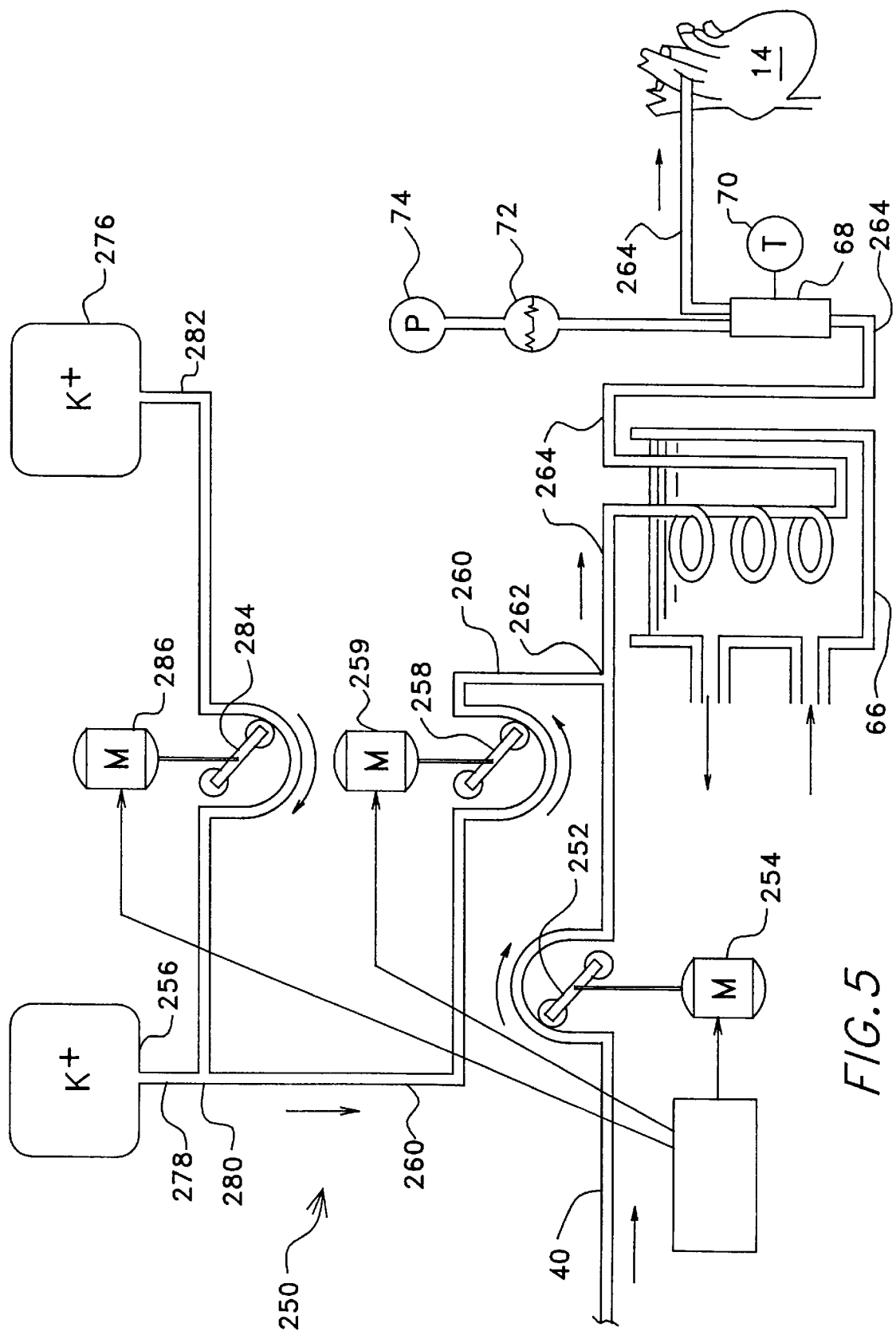
FIG. 5 is a schematic representation of a cardioplegia mixture delivery system in accordance with an alternative preferred embodiment of the present invention.

FIG. 5 is a schematic illustration of another preferred embodiment of a cardioplegia circuit 250 in accordance with the present invention. The arterial blood diversion tubing 40 is installed in the raceway of cardioplegia pump 252 which is driven by a cardioplegia pump motor 254 and is connected to a cardioplegia mixture mixing junction 262. A first source of relatively low concentration crystalloid solution 256 is provided and a second source of relatively high concentration crystalloid solution 276 is also provided. The first source of crystalloid solution 256 is connected by a first crystalloid tubing 278 to a crystalloid mixing junction 280. The second source of crystalloid solution 276 is connected to the crystalloid mixing junction 280 by a second crystalloid tubing 282. A crystalloid concentration control pump 284 and associated concentration control pump motor 286 are provided, with the second crystalloid tubing 282 installed in the raceway of the crystalloid concentration control pump 284. A blended crystalloid tubing 260 interconnects the crystalloid mixing junction 280 with the cardioplegia mixture mixing junction 262. The blended crystalloid tubing 260 is installed in the raceway of a crystalloid pump 258 which is rotatively driven by a crystalloid pump motor 259.

A cardioplegia tubing 264 extends from the cardioplegia mixture mixing junction 262 to the patient's heart 14 to deliver cardioplegia mixture to the heart. Interposed in the cardioplegia tubing are a heat exchanger 66 and bubble trap 68 with associated temperature sensor 70, pressure isolation pod 72 and pressure sensor 74, as previously described. Diverted arterial blood is delivered by the cardioplegia pump 252, and relatively low concentration crystalloid solution flows from the first source of crystalloid solution 256 to the crystalloid mixing junction 280. The crystalloid control pump 286 moves crystalloid solution at a relatively high concentration from the second source of crystalloid solution 276 to the crystalloid mixing junction 280 where a blended crystalloid solution is produced. The blended crystalloid solution is conveyed through the blended crystalloid tubing 260 by the action of the crystalloid pump 258 driven by the crystalloid pump motor 259 and delivered to the cardioplegia blending junction 262 where it is blended with the diverted arterial blood. From the cardioplegia mixture mixing junction 262, the cardioplegia mixture comprising the diverted arterial blood and the blended crystalloid solution is delivered through the cardioplegia tubing 264 to the patient's heart 14.

The total rate volume of cardioplegia solution delivered to the heart 14 can be set by the perfusionist or a control device 251 by adjusting the speed of the pump motor 254 and cardioplegia pump 252 to adjust the amount of diverted arterial blood delivered into the cardioplegia mixture and by adjusting the speed of the crystalloid pump 258 and crystalloid pump motor 259 to control the total amount of blended crystalloid delivered to the mixing junction 262. The total flow of cardioplegia mixture to the heart 14 will be the sum of the diverted arterial blood flow and the flow of blended crystalloid solution. The dilution factor of the cardioplegia mixture will be determined by the ratio of the speeds, and therefore the flow rates, of the crystalloid pump 258 and cardioplegia pump 252. To adjust the concentration of crystalloid in the cardioplegia solution without altering the total volume flow or dilution of the arterial blood in the cardioplegia mixture, the perfusionist or control device 251 merely adjusts the speed of the cardioplegia concentration control pump motor 286 and thus the flow rate of the cardioplegia concentration control pump 284.

Thus, when the crystalloid concentration control pump 284 is not rotating, all of the crystalloid solution in the blended crystalloid solution tubing 260 is from the first source of crystalloid solution 256 and is, therefore, at the relatively low concentration found in the first source of crystalloid solution 256. By actuating and increasing speed of the crystalloid concentration control pump motor 286, and thus the flow rate of the crystalloid concentration control pump 284, higher concentration crystalloid solution is delivered from the second source of crystalloid solution 276, through the second crystalloid tubing 282, to the crystalloid mixing junction 280, thus raising the concentration of the blended crystalloid solution in the blended crystalloid tubing 260 which is ultimately delivered to the cardioplegia mixing junction 262.

Conversely, because the total flow of blended crystalloid solution is fixed by the setting of the crystalloid pump 258, any crystalloid which is delivered to the crystalloid mixing junction 280 by the crystalloid concentration pump 284 from the second source of crystalloid solution 276 will displace an equal flow of lower concentration crystalloid solution from the first source of crystalloid solution 256. Conversely, by reducing the speed of the crystalloid concentration control pump motor 286, and thus the flow rate of the crystalloid concentration control pump 284, the concentration of the blended crystalloid solution in the blended crystalloid tubing 260 and thus in the cardioplegia mixture can be reduced. These adjustments in crystalloid solution concentration in the resulting cardioplegia mixture are thus made without affecting either the aggregate flow rate of cardioplegia mixture to the heart 14 or the dilution of the diverted arterial blood by crystalloid solution. The control device 251 or perfusionist would limit the flow rate of the crystalloid concentration control pump 285 to be equal to or less than the flow rate of the crystalloid pump 258 to prevent flow of crystalloid solution from the second source of crystalloid solution 276 to the first source of crystalloid solution 256.

It is contemplated that a standard automatic control system 251 be employed to control the respective speeds of the crystalloid pump 258 and cardioplegia pump 252, specifically a central controller device, probably computer software, which regulates the speeds of both the cardioplegia pump motor 254 and the crystalloid pump motor 259. This control system 251 is contemplated for use with all the embodiments described herein.

Figure 6:
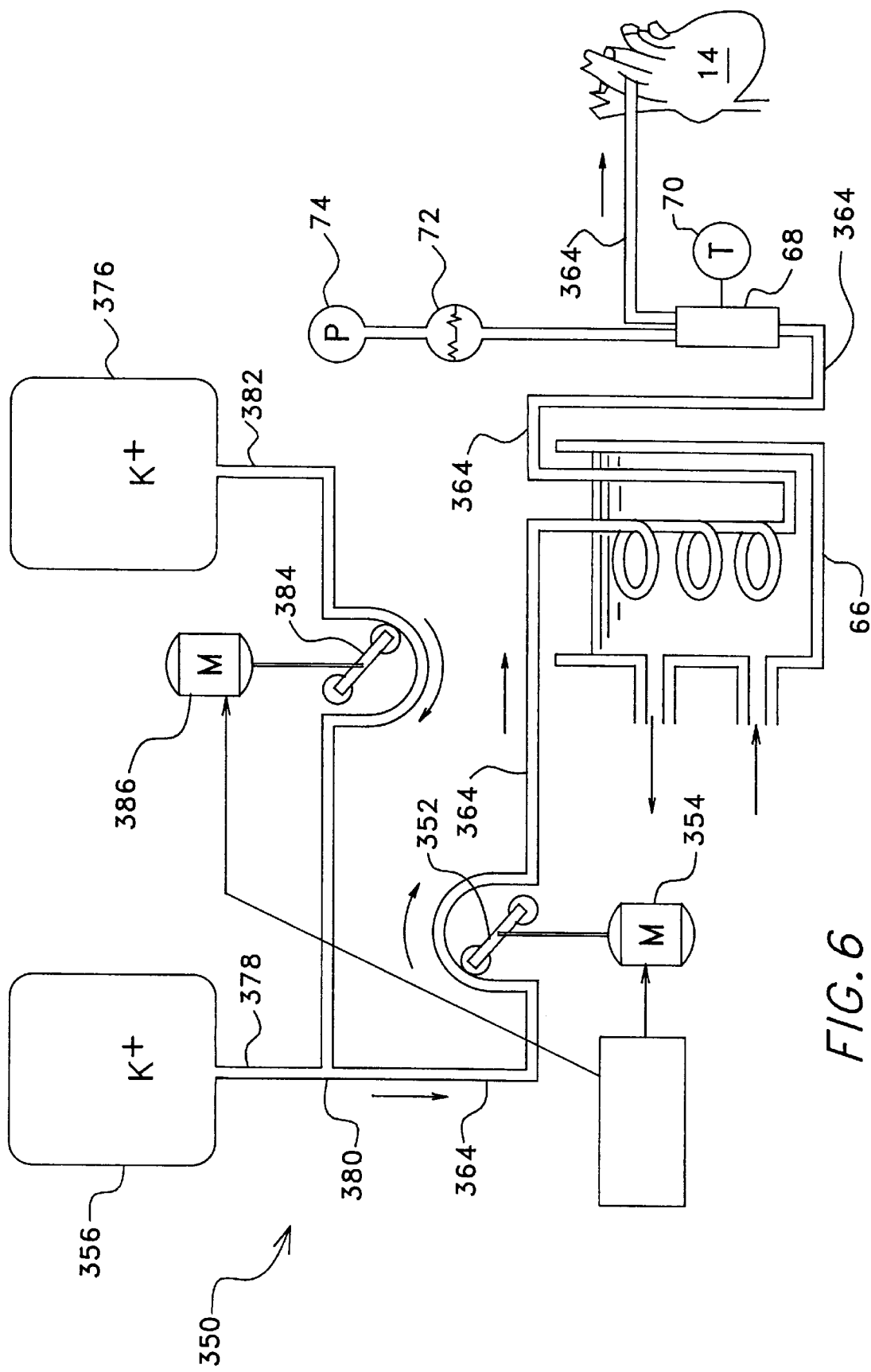
FIG. 6 is a schematic representation of a cardioplegia mixture delivery system in accordance with another alternative preferred embodiment of the present invention.

FIG. 6 illustrates another alternative preferred embodiment of cardioplegia circuit 350 of the present invention. In the embodiment of FIG. 6 no arterial blood is diverted to the cardioplegia circuit 350. The cardioplegia circuit 350 comprises a first source of relatively low concentration crystalloid solution 356 and a second source of relatively high concentration crystalloid solution 376. The relatively low concentration crystalloid solution is delivered through a first crystalloid tubing 378 to a crystalloid mixing junction 380. Relatively high concentration crystalloid solution is delivered to the crystalloid mixing point 380 from the second source of crystalloid solution 376 through a second crystalloid tubing 382 which is installed in the raceway of a crystalloid concentration control pump 384 driven by a crystalloid concentration control pump motor 386. The crystalloid concentration control pump 384 propels and controls the flow of the relatively high concentration crystalloid from the second source of crystalloid solution 376 to the crystalloid mixing junction 380. Blended crystalloid solution is conveyed in a cardioplegia tubing 364 from the crystalloid mixing junction 380 to the heart 14 of the patient. A cardioplegia pump 352 with cardioplegia pump motor 354 is provided and the cardioplegia tubing 364 is installed in the raceway of the cardioplegia pump 352. A cardioplegia heat exchanger 66 and bubble trap 68 with associated temperature sensor 70, pressure isolation pod 72 and pressure sensor 74 are provided interposed in the cardioplegia line 364 as previously described. In this case, the blended crystalloid solution is delivered directly to the heart 14 of the patient without dilution with the diverted arterial blood. The flow rate of blended crystalloid solution is determined by the perfusionist or a control device 351 by setting the speed of the cardioplegia pump motor 354 which in turn controls the flow rate induced by the cardioplegia pump 352.

The concentration of the crystalloid delivered to the heart is established by the perfusionist or control device 351 by activating and establishing the speed of the crystalloid concentration control pump motor 386 and pump 384, which in turn establishes the flow rate of the relatively higher concentration crystalloid solution from the second source of crystalloid solution 376. When the flow rate of the crystalloid concentration control pump 384 is set at a relatively low rate or off, the concentration of the crystalloid solution delivered to the heart will be the same as or nearly the same as the concentration of the crystalloid solution from the first source of the crystalloid solution 356. By increasing the flow of the crystalloid concentration control pump 384 relatively more of the relatively higher concentration crystalloid solution from the second source of crystalloid solution 376 will be included in the blended crystalloid solution flowing through the cardioplegia line 364, thus increasing the potassium or arresting agent concentration of that blended solution. The control device 351 or perfusionist would limit the flow rate of the crystalloid concentration control pump 385 to be equal to or less than the flow rate of the cardioplegia pumps 352 to prevent flow or crystalloid solution from the second source of crystalloid solution 376 to the first source of crystalloid solution 356. Thus, the perfusionist or control device 351 can control the concentration of the crystalloid solution delivered to the heart independent of the flow rate at which the crystalloid solution is delivered.

Equation (1) has been devised for calculating the resultant concentration of crystalloid solution ($C_R$) in the cardioplegia mixture:

$$C_R = \frac{\frac{C_S}{Z} + \frac{C_1}{R_{BC}} + \frac{C_2 - C_1}{R_{B2}}}{\frac{1}{Z} + \frac{1}{R_{BC}}} \qquad (1)$$

In Equation (1), $C_1$ represents the concentration of cardioplegia inducing component in the first crystalloid solution; $C_2$ represents the concentration of cardioplegia inducing component in the second solution; $C_s$ stands for the concentration of cardioplegia inducing component in the diverted arterial blood; Z is a hematocrit correction factor, or $$\frac{1}{1 - RCVF},$$

where RCVF is the red cell volume fraction; $R_{BC}$ is the ratio of the arterial blood flow rate ($Q_B$) to the total combined crystalloid solution flow rate ($Q_C$), or $Q_B/Q_C$; and $R_{B2}$ is the ratio of the blood flow rate ($Q_B$) to the flow rate of the second crystalloid solution ($Q_2$), or $Q_B/Q_2$.

Equation 2 represents a method of calculating the resulted concentration ($C_R$) stated in terms of the crystalloid concentrations of the first and second solutions and their respective flow rate:

$$C_R = \frac{\frac{Q_B}{Z}C_S + Q_C C_C}{\frac{Q_B}{Z} + Q_C} \qquad (2)$$

where $C_C$ is the resultant crystalloid concentration of the combined first and second solutions. $C_C$ in turn, is equal to the sum of the products of the solution respective flow rates and concentrations, divided by the sum of the solutions' flow rates, or $$C_C = \frac{Q_1 C_1 + Q_2 C_2}{Q_1 + Q_2} \qquad (3)$$

where $Q_1$ represents the flow rate of the first crystalloid solution and $Q_2$ is the flow rate of the second crystalloid solution. $Q_1$ can also be determined by subtracting $Q_2$ from $Q_C$, as noted above:

$$Q_1 = Q_C - Q_2, \text{ where } Q_C = Q_B/R_{BC} \qquad (4)$$

Figure 7:
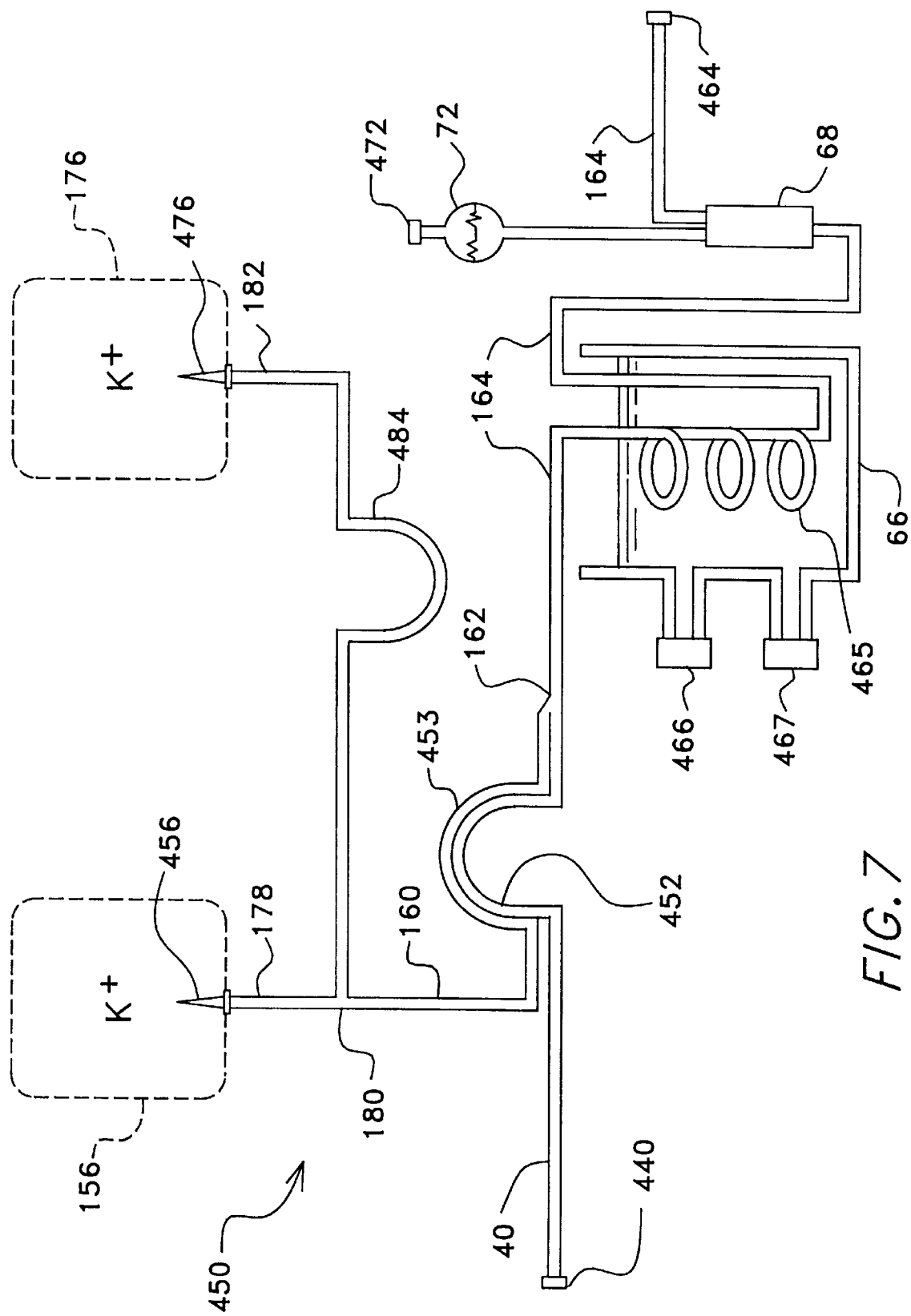
FIG. 7 is a schematic representation of a disposable tubing set adapted for use as a component of the preferred embodiment of the present invention represented in FIG. 4.

In use, the invention will typically be made up of single use disposable and consumable components, such as tubing and other elements which do or potentially can come in contact with the patient's bodily fluids and multiple use components, such as the pumps and their drivers. FIG. 7 illustrates the disposable elements of the system which are typically referred as a cardioplegia tubing set. FIG. 7 illustrates a typical cardioplegia tubing set adapted for use with the present invention. The cardioplegia tubing set illustrated in FIG. 7 is adapted for use with the preferred embodiment of the invention represented in FIG. 4. It will be apparent to those skilled in the art, however, that tubing sets adapted for use with the embodiments of the preferred invention illustrated in FIGS. 5 and 6, as well as other embodiments of the invention, are within the scope of the present invention. The cardioplegia disposable tubing set comprises the arterial blood diversion tubing 40 which extends from a diversion tubing connector 440, which may be a luer connector or any other suitable type of medical tubing connector, to the cardioplegia mixture mixing junction 162. The diversion tubing connector 440 is adapted for connecting the cardioplegia tubing set to the tubing set of the cardiopulmonary support circuit. Alternatively, in lieu of the diversion tubing connector 440, the arterial blood diversion tubing 40 may be connected directly to the heart lung tubing cardiopulmonary support circuit 10. Intermediate the diversion tubing connector 440 and the cardioplegia mixture mixing junction 162 is a pump header portion 452 adapted for inter-fitting with the raceway and rotor of a peristaltic pump. The cardioplegia line 164 extends from the cardioplegia mixture mixing junction 162 to a cardioplegia cannula connector 464. In lieu of the cardioplegia cannula connector 464, cardioplegia cannula may be directly connected to the cardioplegia line 164. Intermediate the cardioplegia mixture mixing junction 162 and the cardioplegia cannula connector 464 is provided a heat exchange portion 465, typically tubing, which forms a part of the heat exchanger 66. Also provided in the cardioplegia line 164 intermediate the cardioplegia mixture mixing junction 162 and the cardioplegia canula connector 464, may be a bubble trap 68 and pressure isolation pod 72 with a connector, such as a luer connector 472 for connection to the pressure sensor (not shown). The heat exchanger 66 may comprise a disposable heat exchanger or may comprise a disposable portion and a non-disposable portion. The heat exchanger further comprises connectors 466, 467 to supply and remove cooling fluid, such as water, from the heat exchanger 66. The cooling fluid connectors 466, 467 may comprise hansen connector as is well known. The blended crystalloid tubing 160 extends from the cardioplegia mixture mixing junction 162 to the crystalloid mixing junction 280 and includes intermediate the cardioplegia mixture mixing junction 162 and the crystalloid mixing junction 180 a pump header portion 453 adapted for fitting in the raceway of the same peristaltic pump, as is the pump header portion 452 of the arterial blood diversion tubing 40. Extending from the crystalloid mixing junction 280 is a first crystalloid tubing 278 which is terminated in a first crystalloid connector 456 which may be of the typical solution bag spike type, or may be a luer or hansen connector, or may be a pre-made connection to the first source of crystalloid solution 156. If the first crystalloid connector 456 is a pre-made connector, the first source of crystalloid solution 156 forms a part of the disposable cardioplegia tubing set 450.

Extending from the crystalloid mixing junction 180 is the second crystalloid solution tubing 182 which is terminated in a second crystalloid connector 476. The second crystalloid connector may be of the typical bag spike type, may be a luer connector, or may be a pre-made connection to the second source of crystalloid solution 176. If the second crystalloid connector is a pre-made connection to the second source of crystalloid solution 176, the second source of crystalloid solution 176 forms a portion of the disposable cardioplegia tubing set 450. Intermediate of the crystalloid mixing junction 180 and the second crystalloid connector 476 is a pump header portion 484 of the second crystalloid tubing 182 adapted for inter-fitting with the raceway and rotor of the crystalloid concentration control pump (not shown).

It will be apparent to those skilled in the art that there are many variations possible within the scope of the preferred embodiments and the following claims. Further, the preferred embodiments described are by way of example only and it would be appreciated that numerous variations and modifications may be effected without departing from the spirit or scope of the invention. The appended claims are intended to cover all such modifications and variations.

What is claimed is:

1. A method of preparing a cardioplegia mixture comprising:

providing a first source of a first crystalloid solution which includes a cardioplegia inducing component at a concentration;

providing a second source of a second crystalloid solution which includes the cardioplegia inducing component at a different concentration than the concentration in the first crystalloid solution;

flowing first crystalloid solution from the first source of crystalloid cardioplegia solution;

flowing second crystalloid solution from the second source of crystalloid solution;

combining the flowing first crystalloid solution with the flowing second crystalloid solution;

establishing a total volume flow rate of the combined first and second crystalloid solutions from the first and second sources of crystalloid solution;

establishing a volume flow rate of the second crystalloid solution from the second source of crystalloid solution; and allowing the flow rate of first crystalloid solution from the first source of crystalloid solution to self adjust to be equal to the established total volume flow rate minus the established volume flow rate of the second crystalloid solution.

2. The method of claim 1 wherein:

the concentration of the cardioplegia inducing component of the first crystalloid solution is relatively low; and the concentration of the cardioplegia inducing component in the second crystalloid solution is relatively higher than the concentration of the cardioplegia inducing component in the first crystalloid solution.

3. The method of claim 2 wherein the step of providing the first source of a first crystalloid solution comprises:

selecting the concentration of the cardioplegia inducing component in the first crystalloid solution to achieve a value less than or equal to the minimum desired concentration of the cardioplegia inducing component in the cardioplegia mixture when the crystalloid solution included in the cardioplegia mixture is only the first crystalloid solution.

4. The method of claim 2 wherein the step of providing the second source of a second crystalloid solution further comprises:

selecting the concentration of the cardioplegia inducing component in the second solution to achieve a value greater than or equal to the maximum desired concentration of the cardioplegia inducing component in the cardioplegia mixture when the crystalloid solution included in the cardioplegia mixture is only the second crystalloid solution.

5. The method of claim 1 wherein the step of establishing a total volume flow rate of the combined first and second crystalloid solutions from the first and second sources of crystalloid solution further comprises: establishing a predetermined volume flow rate of combined first and second crystalloid solutions.

6. The method of claim 1 wherein the step of establishing a total volume flow rate of the combined first and second crystalloid solutions from the first and second sources of crystalloid solution further comprises:

selecting the volume flow rate of combined first and second crystalloid solutions from a continuously variable range of flow rates.

7. The method of claim 1 wherein the step of establishing a volume flow rate of the second crystalloid solution from the second source of crystalloid solution further comprises:

selecting the volume flow rate of the second crystalloid solution from a continuously variable range of flow rates.

8. The method of claim 1 further comprising:

diverting a flow of blood from a cardiopulmonary circuit;

establishing a volume flow rate of the diverted blood; and combining the flowing diverted blood with the flowing combined first and second crystalloid solutions from the first and second sources of crystalloid solution.

9. The method of claim 8 wherein the step of establishing the volume flow rate of the diverted oxygenated blood further comprises:

establishing a predetermined volume flow rate of diverted oxygenated blood.

10. The method of claim 8 wherein the step of establishing the volume flow rate of the diverted oxygenated blood further comprises:

selecting the volume flow rate of diverted blood from a continuously variable range of flow rates.

11. The method of claim 8 wherein the step of providing the first source of a first crystalloid solution comprises:

selecting the concentration of the cardioplegia inducing component in the first solution to achieve a value less than or equal to the minimum desired concentration of the cardioplegia inducing component in the cardioplegia mixture when the crystalloid solution included in the cardioplegia mixture is only the first crystalloid solution.

12. The method of claim 8 wherein the step of providing the second source of a second crystalloid solution further comprises:

selecting the concentration of the cardioplegia inducing component in the second solution to achieve a value greater than or equal to the maximum desired concentration of the cardioplegia inducing component in the cardioplegia mixture when the crystalloid solution included in the cardioplegia mixture is only the second crystalloid solution.

13. The method of claim 8 wherein the step of establishing a total volume flow rate of the combined first and second crystalloid solutions from the first and second sources of crystalloid solution further comprises:

establishing a predetermined volume flow rate of the combined first and second crystalloid solutions.

14. The method of claim 8 wherein the step of establishing a total volume flow rate of the combined first and second crystalloid solutions from the first and second sources of crystalloid solution further comprises:

selecting the volume flow rate of the combined first and second crystalloid solutions from a continuously variable range of flow rates.

15. The method of claim 8 wherein the step of establishing a volume flow rate of the second crystalloid solution from the second source of crystalloid solution further comprises:

selecting the volume flow rate of the second crystalloid solution from a continuously variable range of flow rates.

16. The method of claim 8 wherein the steps of establishing the volume flow rate of the diverted blood and establishing the volume flow rate of the combined first and second crystalloid solutions further comprise:

selecting and establishing a predetermined ratio between the volume flow rate of the diverted oxygenated blood and the combined first and second crystalloid solutions.

17. The method of claim 1 further comprising:

diverting a flow of blood from a cardiopulmonary circuit;

combining the flowing diverted blood with the flowing combined first and second crystalloid solutions from the first and second sources of crystalloid solution;

selecting and establishing a predetermined ratio between the volume flow rate of the diverted oxygenated blood and the combined first and second crystalloid solutions;

simultaneously selecting and establishing a volume flow rate of combined first and second crystalloid solutions and a volume flow rate of the diverted oxygenated blood at the predetermined ratio from a continuously variable range of flow rates; and selecting and establishing the volume flow rate of the second crystalloid a continuously variable range of flow rates; wherein the concentration of the cardioplegia inducing component of the first crystalloid solution is relatively low and is selected to achieve a value less than or equal to the minimum desired concentration of the cardioplegia inducing component in the cardioplegia mixture when the crystalloid solution included in the cardioplegia mixture is only the first crystalloid solution;

the concentration of the cardioplegia inducing component in the second crystalloid solution is relatively higher than the concentration of the cardioplegia inducing component in the first crystalloid solution and is selected to achieve a value greater than or equal to the maximum desired concentration of the cardioplegia inducing component in the cardioplegia mixture when the crystalloid solution included in the cardioplegia mixture is only the second crystalloid solution.

18. The method of claim 17 further comprising:

adjusting the temperature of the cardioplegia mixture.

* * * * *